United States Patent [19]

Schliebs et al.

[11] 3,970,586
[45] July 20, 1976

[54] PERFLUOROALKANE SULFONAMIDO-ALKANE PHOSPHONIC AND PHOSPHONIC ACID DERIVATIVES

[75] Inventors: Reinhard Schliebs, Cologne; Manfred Wechsberg, Opladen; Johann Nikolaus Meussdoerffer, Blecher, all of Germany

[73] Assignee: Bayer Aktiengesellschaft, Leverkusen, Germany

[22] Filed: May 7, 1975

[21] Appl. No.: 575,097

[30] Foreign Application Priority Data

May 18, 1974  Germany............................ 2424243

[52] U.S. Cl................................ 252/355; 260/944; 260/924; 260/502.5; 260/290 HL
[51] Int. Cl.²....................... B01F 17/14; C07F 9/09
[58] Field of Search............... 260/556 F, 955, 944, 260/502.5; 252/355

[56] References Cited
UNITED STATES PATENTS

| | | | |
|---|---|---|---|
| 2,759,019 | 8/1956 | Brown et al. | 260/556 F |
| 3,094,547 | 6/1963 | Heine | 252/355 |
| 3,870,771 | 3/1975 | Golborn et al. | 260/944 |

*Primary Examiner*—Benjamin R. Padgett
*Assistant Examiner*—David Leland
*Attorney, Agent, or Firm*—Burgess, Dinklage & Sprung

[57] ABSTRACT

An ω-perfluoroalkane sulfonamido-alkane phosphonic or phosphinic acid or salt of the formula

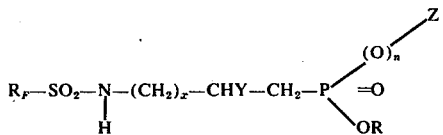

in which
$R_F$ is a perfluoroalkyl radical with from 1 to 12 carbon atoms;
$x$ and $n$ each independently is 0 or 1,
Y is hydrogen or a lower aliphatic radical with up to 5 carbon atoms,
Z is an aliphatic radical with up to 5 carbon atoms, a cycloaliphatic, araliphatic or aromatic radical, and
R is hydrogen, an alkali metal, alkaline earth metal or ammonium radical.

The compounds are useful as surfactants in depressing the surface tension of water.

7 Claims, No Drawings

PERFLUOROALKANE SULFONAMIDO-ALKANE PHOSPHONIC AND PHOSPHINIC ACID DERIVATIVES

This invention relates to new perfluoroalkane sulfonamido-alkane phosphonic acid and phosphinic acid derivatives, to a process for their production and to their use as surfactants.

The class of compounds according to the invention corresponds to the general formula:

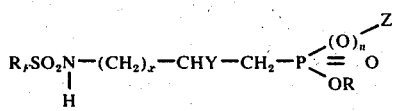

in which
- $R_F$ is a perfluoroalkyl radical with from 1 to 12 carbon atoms,
- $x$ and $n$ each independently is 0 or 1,
- Y is hydrogen or a lower aliphatic radical with up to 5 carbon atoms,
- Z is an aliphatic radical with up to 5 carbon atoms, a cycloaliphatic, araliphatic or aromatic radical, and
- R is hydrogen, an alkali metal, alkaline earth metal or ammonium radical.

Preferably $R_F$ is a perfluoroalkyl radical with from 4 to 8 carbon atoms; Y is hydrogen or methyl; Z is alkyl of up to 4 carbon atoms, cyclopentyl, cyclohexyl, benzyl, phenethyl, phenyl or tolyl; and R is hydrogen, sodium, potassium, ammonium, trimethylammonium, triethylammonium or pyridinium.

The compounds according to the invention may be prepared in accordance with the following general equation:

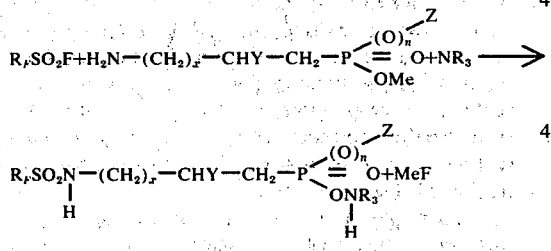

(Me = Na, K)

The ω-aminoalkane phosphonic acid and phosphinic acid derivatives used as starting compounds can be prepared in accordance with German Offenlegungeschrift DOS No. 2,032,712 while the perfluoroalkane sulfonic acid fluorides can be obtained by electrofluorination of the corresponding alkane sulfonic acid halides in accordance with German Offenlegungsschrift DOS No. 1,912,738.

The reaction is best carried out in the presence of a dry, polar solvent, for example methanol.

The process according to the invention is carried out in anhydrous, polar solvents, for example alcohols, which are able on the one hand to dissolve both the starting compounds and also the required end products, but which on the other hand enable the fluorides additionally formed to be separated off. The exclusion of moisture is intended to prevent the perfluoroalkane sulfonyl fluoride from being hydrolyzed into the corresponding ammonium perfluoroalkane sulfonates. The use of the aforementioned solvents also enables the heat of reaction to be dissipated without difficulty. Although the reactions are carried out under normal pressure, they may also be carried out under excess pressure, especially in cases where the low-boiling perfluoroalkane sulfonyl fluorides are used. The reaction temperature can be in the range of from about −50°C to about 200°C, although it is preferably in the range of about 20° to 100°C.

The hydrogen fluoride generally formed to begin with during the reaction of the perfluoroalkane sulfonyl fluorides with primary or secondary amines:

($R^1$ = alkyl; $R^2$ = H or alkyl) has to be taken up by suitable acid acceptors, generally tertiary amines such as triethyl amine or pyridine.

However, it has surprisingly been found, in cases where the aminoalkane phosphonic acid/phosphinic acid derivatives obtainable in accordance with DOS No. 2,032,712 are used, that the hydrogen fluoride formally otained to begin with does not react with the tertiary amine added to form a trialkyl ammonium fluoride, but instead reacts with the alkali metal of the phosphonate or phosphinate to form alkali metal fluoride and the corresponding ammonium phosphonate or ammonium phosphinate. The alkali metal fluoride formed can readily be separated off quantitatively where the corresponding alkali metal salt of the phosphonic or phosphinic acid has been used.

The corresponding perfluoroalkane sulfonamidoalkane phosphonic acid or phosphinic acid derivatives are then obtained following removal of the solvent used. The following are examples of the compounds according to the invention:

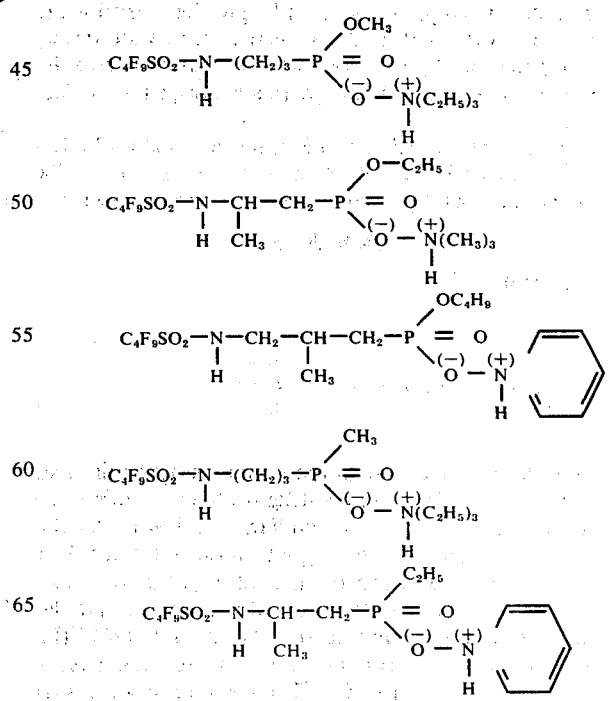

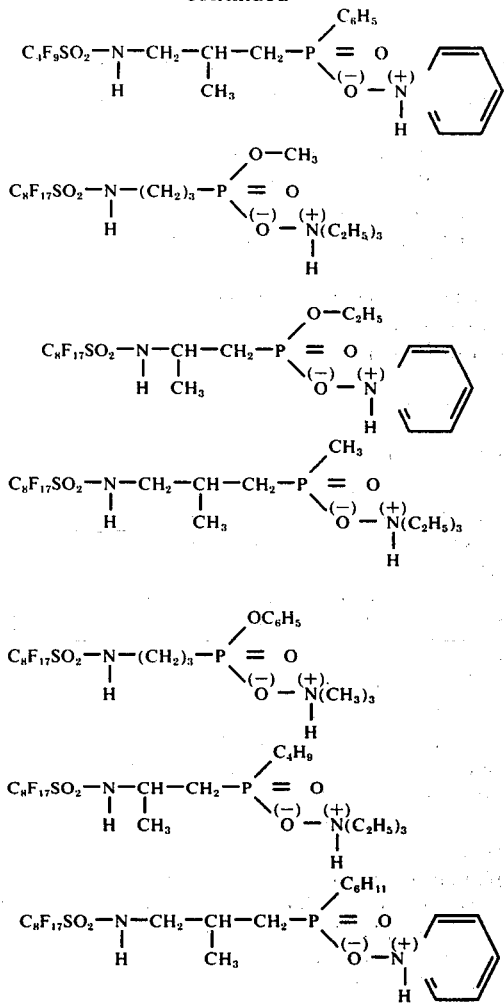

Even by comparison with known fluorine-based surfactants, the compounds according to the invention are powerful surfactants and may be used for a wide variety of applications by virtue of their extremely good solubility in water and other organic solvents, such as alcohols.

The invention is illustrated in more detail in the following Examples, the surface-active properties of the compounds being demonstrated in comparison tests:

EXAMPLE 1

0.1 mole (17.5 g) of

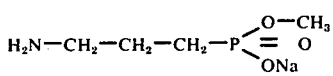

the sodium salt of ω-aminopropane phosphonic acid methyl ester and 0.12 mole (12 g) of triethyl amine, are introduced into 125 ml of methanol, followed by the gradual addition with stirring at around 60°C of 0.11 mole (55 g) of perfluorooctane sulfonyl fluoride. The reaction is complete after about 15 minutes, and the sodium fluoride precipitated can be separated off. The clear solution is subsequently concentrated by evaporation in vacuo to dryness. The residue obtained is slightly hygroscopic. It contains at most 0.05% of inorganic fluoride.

EXAMPLE 2

0.1 mole of the sodium salt of ω-aminopropane phosphonic acid methyl ester, 0.1 mole of triethyl amine and 0.1 mole (30.2 g) of perfluorobutane sulfonyl fluoride are reacted in 125 ml of methanol in the same way as in Example 1. The slightly exothermic reaction is complete after about 10 minutes and the NaF formed can be separated off again. The required compound is obtained after the solvent has been distilled off.

EXAMPLE 3

0.1 mole (15.9 g) of

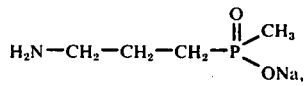

the sodium salt of ω-aminopropane methane phosphinate, and 0.12 mole (12 g) of triethyl amine are introduced into 125 ml of absolute methanol, followed by the gradual addition with stirring at around 60°C of 0.11 mole (55 g) of perfluorooctane sulfonyl fluoride, in the same way as in Example 1. The reaction is complete after about 15 minutes and the NaF formed can be quantitatively separated off, for example by centrifuging. The required compound is obtained as a residue after the solution has been concentrated by evaporation.

Measurement of Surface Tension

Measurement of the surface tension of the compound prepared in accordance with Example 1 in water at a temperature of 20°C produced a maximum reduction of from 72 dyn/cm to 17.7 dyn/cm for a concentration of 1.0 g per liter of water.

Since the compounds according to the invention are used as surface-active substances, they are best compared with products which are known to show good surface-active properties. One such product is potassium perfluorooctane sulfonate which can reduce the surface tension of water to 23.0 dyn/cm for a concentration of 4.0 g per liter.

Accordingly, the substances according to the invention give lower surface-tension values for lower concentrations but, at the same time, with considerably better solubility in water or, for example, even in alcohols.

It will be appreciated that the instant specification and examples are set forth by way of illustration and not limitation, and that various modifications and changes may be made without departing from the spirit and scope of the present invention.

What is claimed is:

1. An ω-perfluoroalkane sulfonamido-alkane phosphonic or phosphinic acid or salt of the formula

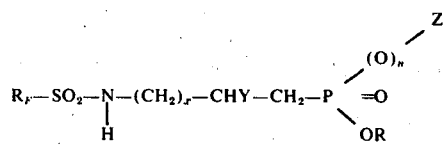

in which

R_F is a perfluoroalkyl radical with from 1 to 12 carbon atoms, x and n each independently is 0 or 1, Y is hydrogen or a lower aliphatic radical with up to 5 carbon atoms, Z is an aliphatic radical with up to 5 carbon atoms, a cycloaliphatic, araliphatic or aromatic radical, and R is hydrogen, an alkali metal, alkaline earth metal, ammonium radical or substituted ammonium radical.

2. An acid or salt according to claim 1, wherein

R_F is a perfluoroalkyl radical with from 4 to 8 carbon atoms,

Y is hydrogen or methyl,

Z is alkyl of up to 4 carbon atoms, cyclopentyl, cyclohexyl, benzyl, phenethyl, phenyl or tolyl, and R is hydrogen, sodium, potassium, ammonium, trimethylammonium, triethylammonium or pyridinium.

3. A salt according to claim 1 of the formula

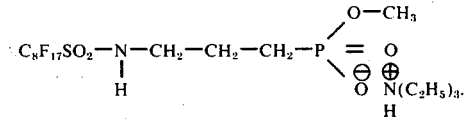

4. A salt according to claim 1 of the formula

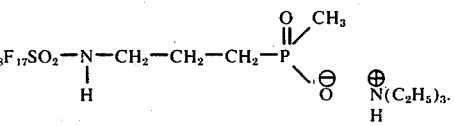

5. A process for the production of a compound according to claim 1, comprising reacting a perfluoroalkane sulfonyl fluoride of the formula $R_F$—$SO_2$—F with an ω-aminoalkane phosphonic acid or phosphinic acid or salt of the formula

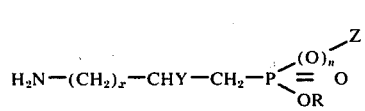

in the presence of a tertiary amine.

6. A surface-active composition comprising a surface-active amount of a compound according to claim 1 and a liquid diluent.

7. The method of reducing the surface tension of a liquid which comprises adding thereto a surface-active amount of a compound according to claim 1.